(12) United States Patent
Peretz et al.

(10) Patent No.: US 6,946,131 B2
(45) Date of Patent: *Sep. 20, 2005

(54) HEPARANASE ACTIVITY NEUTRALIZING ANTI-HEPARANASE MONOCLONAL ANTIBODY

(75) Inventors: Tuvia Peretz, Hasharon (IL); Daphna Miron, Rehovot (IL); Yinon Shlomi, Rehovot (IL); Iris Pecker, Rishon LeZion (IL); Maty Ayal-Hershkovitz, Herzlia (IL); Israel Vlodavsky, Mevaseret Zion (IL); Yael Friedmann, Mevaseret Zion (IL)

(73) Assignees: InSight Biopharmacenticals Ltd., Rehovot (IL); Hadasit Medical Research Services and Development Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/368,044

(22) Filed: Feb. 19, 2003

(65) Prior Publication Data

US 2003/0181687 A1 Sep. 25, 2003

Related U.S. Application Data (60) Division of application No. 09/186,200, filed on Nov. 4, 1998, now Pat. No. 6,562,950, which is a continuation-in-part of application No. 09/071,739, filed on May 1, 1998, now Pat. No. 6,177,545, which is a continuation-in-part of application No. 08/922,170, filed on Sep. 2, 1997, now Pat. No. 5,968,822.

(51) Int. Cl.$^7$ ............................................. A61K 39/395
(52) U.S. Cl. ............................... 424/141.1; 424/142.1; 424/146.1
(58) Field of Search .......................... 424/141.1, 142.1, 424/146.1

(56) References Cited

U.S. PATENT DOCUMENTS 5,736,137 A * 4/1998 Anderson et al. ........ 424/133.1

OTHER PUBLICATIONS

Vlodavsky et al. Invasion Metastasis 1994,–95 14: 290–302.*
Nakajima et al. J. Cell. Biochem. 1988, 36: 157–167.*
Lider et al. J. Clin. Invest. 1989, 83: 752–756.*
Parish et al. Int. J. Cancer 1987, 40: 511–518.*

* cited by examiner

Primary Examiner—Christina Chan
Assistant Examiner—Marianne DiBrino (57) ABSTRACT

A method of treating a condition associated with heparanase expression by administering a heparanase activity neutralizing monoclonal anti-heparanase antibody, the monoclonal anti-heparanase antibody being for neutralizing heparanase catalytic activity.

6 Claims, 2 Drawing Sheets

SEQUENCE LISTING

```
<160> NUMBER OF SEQ ID NOS: 1
<210> SEQ ID NO 1
<211> LENGTH: 543
<212> TYPE: PRT
<213> ORGANISM: Homo sapiens

<400> SEQUENCE: 1

Met Leu Leu Arg Ser Lys Pro Ala Leu Pro Pro Pro Leu Met Leu Leu
1               5                   10                  15

Leu Leu Gly Pro Leu Gly Pro Leu Ser Pro Gly Ala Leu Pro Arg Pro
                20                  25                  30

Ala Gln Ala Gln Asp Val Val Asp Leu Asp Phe Phe Thr Gln Glu Pro
            35                  40                  45

Leu His Leu Val Ser Pro Ser Phe Leu Ser Val Thr Ile Asp Ala Asn
        50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95
```

```
Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Lys Leu Arg Leu Glu Trp
    130                 135                 140

Pro Tyr Gln Glu Gln Leu Leu Arg Glu His Tyr Gln Lys Lys Phe
145                 150                 155                 160

Lys Asn Ser Thr Tyr Ser Arg Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220

Glu Pro Asn Ser Phe Leu Lys Lys Ala Asp Ile Phe Ile Asn Gly Ser
225                 230                 235                 240

Gln Leu Gly Glu Asp Tyr Ile Gln Leu His Lys Leu Leu Arg Lys Ser
                245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
    290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
        355                 360                 365

Leu Gly Leu Ser Ala Arg Met Gly Ile Glu Val Val Met Arg Gln Val
    370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445

Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
            500                 505                 510
```

```
                                    -continued

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
    530                 535                 540
```

HEPARANASE ACTIVITY NEUTRALIZING ANTI-HEPARANASE MONOCLONAL ANTIBODY

This is a divisional of U.S. patent application Ser. No. 09/186,200, filed Nov. 4, 1998 now U.S. Pat. No. 6,562,950, which is a continuation-in-part of U.S. patent application Ser. No. 09/071,739, filed May 1, 1998, now U.S. Pat. No. 6,177,545, issued Jan. 23, 2001, which is a continuation-in-part of U.S. patent application Ser. No. 08/922,170, filed Sep. 2, 1997, now U.S. Pat. No. 5,968,822, issued Oct. 19, 1999.

FIELD AND BACKGROUND OF THE INVENTION

The present invention relates to an anti-heparanase antibody and, more particularly, to a heparanase activity neutralizing monoclonal anti-heparanase antibody.

Heparan sulfate proteoglyeans (HSPGs): HSPGs are ubiquitous macromolecules associated with the cell surface and the extracellular matrix (ECM) of a wide range of cells of vertebrate and invertebrate tissues (1–5). The basic HSPG structure consists of a protein core to which several linear heparan sulfate chains are covalently attached. The polysaccharide chains are typically composed of repeating hexuronic and D-glucosamine disaccharide units that are substituted to a varying extent with N- and O-linked sulfate moieties and N-linked acetyl groups (1–5). Studies on the involvement of ECM molecules in cell attachment, growth and differentiation revealed a central role of HSPGs in embryonic morphogenesis, angiogenesis, metastasis, neurite outgrowth and tissue repair (1–5). The heparan sulfate (HS) chains, unique in their ability to bind a multitude of proteins, ensure that a wide variety of effector molecules cling to the cell surface (4–6). HSPGs are also prominent components of blood vessels (3). In large vessels they are concentrated mostly in the intima and inner media, whereas in capillaries they are found mainly in the subendothelial basement membrane where they support proliferating and migrating endothelial cells and stabilize the structure of the capillary wall. The ability of HSPGs to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of HS may therefore result in disassembly of the subendothelial ECM and hence may play a decisive role in extravasation of normal and malignant blood-borne cells (7–9). HS catabolism is observed in inflammation, wound repair, diabetes, and cancer metastasis, suggesting that enzymes that degrade HS play important roles in pathologic processes.

Involvement of heparanase in tumor cell invasion and metastasis: Circulating tumor cells arrested in the capillary beds of different organs must invade the endothelial cell lining and degrade its underlying basement membrane (BM) in order to escape into the extravascular tissue(s) where they establish metastasis (10). Several cellular enzymes (e.g., collagenase IV, plasminogen activator, cathepsin B, elastase, etc.) are thought to be involved in degradation of the BM (10). Among these enzymes is an endo-β-D-glucuronidase (heparanase) that cleaves HS at specific intrachain sites (7, 9, 11–12). Expression of a HS degrading heparanase was found to correlate with the metastatic potential of mouse lymphoma (11), fibrosarcoma and melanoma (9) cells. The same is true for human breast, bladder and prostate carcinoma cells (U.S. patent application Ser. No. 09/071,739). Moreover, elevated levels of heparanase were detected in sera (9) and urine (U.S. patent application Ser. No. 09/071, 739) of metastatic tumor bearing animals and cancer patients and in tumor biopsies (12). Treatment of experimental animals with heparanase inhibitors such as iaminarin sulfate, markeuly reduced (>90%) the incidence of lung metastases induced by B16 melanoma, Lewis lung carcinoma and mammary adenocarcinoma cells (8, 9, 13), indicating that inhibition of heparanase activity by neutralizing antibodies, when available, may be applied to inhibit tumor cell invasion and metastasis.

Possible involvement of heparanase in tumor angiogenesis: It was previously demonstrated that heparanase may not only function in cell migration and invasion, but may also elicit an indirect neovascular response (15). These results suggest that the ECM HSPGs provide a natural storage depot for bFGF and possibly other heparin-binding growth promoting factors. Heparanase mediated release of active bFGF from its storage within ECM may therefore provide a novel mechanism for induction of neovascularization in normal and pathological situations (6, 18).

Expression of heparanase by cells of the immune system: Heparanase activity correlates with the ability of activated cells of the immune system to leave the circulation and elicit both inflammatory and autoimmune responses.

Interaction of platelets, granulocytes, T and B lymphocytes, macrophages and mast cells with the subendothelial ECM is associated with degradation of heparan sulfate (HS) by heparanase activity (7). The enzyme is released from intracellular compartments (e.g., lysosomes, specific granules, etc.) in response to various activation signals (e.g., thrombin, calcium ionophore, immune complexes, antigens, mitogens, etc.), suggesting its regulated involvement and presence in inflammatory sites and autoimmune lesions. Heparan sulfate degrading enzymes released by platelets and macrophages are likely to be present in atherosclerotic lesions (16). Treatment of experimental animals with heparanase inhibitors markedly reduced the incidence of experimental autoimmune encephalomyelitis (EAE), adjuvant athritis and graft rejection (7, 17) in experimental animals, indicating that the use of neutralizing antibodies to inhibit heparanase activity may inhibit autoimmune and inflammatory diseases (7, 17).

Use of monoclonal antibodies for clinical therapeutics: Monoclonal antibodies (Mabs) are beginning to gain a prominent role in the therapeutics arena. Approximately 80 Mabs are in clinical development which represent over 30% of all biological proteins undergoing clinical trials (20, 24). Market entry of new Mab therapies is expected to be dramatically accelerated. Fueling this growth has been the emergence of technologies to create increasingly human-like (humanized) Mabs, ranging from chimerics to fully human. These new Mabs promise to overcome the human antibody to mouse antibody response (25).

Monoclonal antibodies, which can be viewed as nature's own form of "rational drug design", can offer an accelerated drug-discovery approach for appropriate targets. That is because producing high affinity Mabs that specifically block the activity of an antigen target is usually easier and faster than designing a small molecule with similar activity (23).

Due to their long serum half-life, low toxicity and high specificity, Mabs began to reveal their true therapeutic potential, particularly in oncology, where current therapeutic regimens have toxic side effects that, in many cases, require repetitive dosing in the respective treatment protocols (23).

Until today only two therapeutic Mabs have been approved for sale in the U.S.—the mouse OKT-3 for prevention of organ transplant rejection, and the mouse-human chimeric Fab fragment, for prevention of acute cardiac ischemia following coronary angioplasty (25). Recently, Herceptin, humanized Mab raised against the protooncogene HER-2/neu, has passed Phase III clinical tests in treating breast cancer patients with metastatic disease (23).

In using anti-angiogenesis approach in preventing metastasic disease, Genetech introduced a recombinant humanized Mab to the vascular endothelial growth factor (VEGF). The anti-VEGF rhu Mab was found to be safe and well tolerated in a 25-patient pilot Phase I clinical study (23).

There is thus a widely recognized need for, and it would be highly advantageous to have a heparanase activity anti-heparanase monoclonal antibody.

SUMMARY OF THE INVENTION

It is one object of the present invention to provide heparanase activity neutralizing monoclonal anti-heparanase antibody for inhibition of heparanase activity and a method of preparing same.

It is another object of the present invention to provide a pharmaceutical composition including the antibody for treating a condition associated with heparanase activity, thus to use the antibody as a therapeutic agent.

Thus, according to one aspect of the present invention there is provided a monoclonal antibody elicited by a heparanase protein or an immunogenical portion thereof, the monoclonal antibody specifically inhibits heparanase activity.

According to another aspect of the present invention there is provided a pharmaceutical composition comprising as an active ingredient thereof a monoclonal antibody elicited by a heparanase protein or an immunogenical portion thereof, the monoclonal antibody specifically inhibits heparanase activity, and a pharmaceutical acceptable carrier.

According to further features in preferred embodiments of the invention described below, the heparanase protein or the immunogenical portion thereof is recombinant.

According to still further features in the described preferred embodiments the heparanase activity is of recombinant heparanase or natural heparanase.

According to still further features in the described preferred embodiments the monoclonal antibody is humanized.

According to still further features in the described preferred embodiments at least about 90% of the heparanase activity is abolished by the inhibition when about 1 to about 1–40 ratio of heparanase to antibody is realized.

According to still further features in the described preferred embodiments the monoclonal antibody binds to a C'-terminal portion of heparanase.

According to still another aspect of the present invention there is provided an in vivo or in vitro method of preparing a heparanase activity neutralizing monoclonal anti-heparanase antibody, the method comprising the steps of (a) exposing cells capable of producing antibodies to a heparanase protein or an immonogenical part thereof and thereby generating antibody producing cells; (b) fusing the antibody producing cells with myeloma cells and thereby generating a plurality of hybridoma cells each producing monoclonal antibodies; and (c) screening the plurality of monoclonal antibodies to identify a monoclonal antibody which specifically inhibits heparanase activity.

According to still further features in the described preferred embodiments the method further comprising the step of humanizing the heparanase activity neutralizing monoclonal anti-heparanase antibody.

According to still further features in the described preferred embodiments the immonogenical part of the heparanase protein includes a C'-terminal portion of the heparanase protein.

According to still another aspect of the present invention there is provided a method of treating a condition associated with heparanase expression comprising the step of administering a heparanase activity neutralizing monoclonal anti-heparanase antibody, the monoclonal anti-heparanase antibody being for neutralizing heparanase catalytic activity.

According to still further features in the described preferred embodiments the condition is associated with altered function of a HSPG associated biological effector molecule.

According to still further features in the described preferred embodiments the HSPG associated biological effector molecule is selected from the group consisting of a growth factor, a chemokine, a cytokine and a degradative enzyme.

According to still further features in the described preferred embodiments the growth factor is selected from the group consisting of HGH, FGF and VEGF.

According to still further features in the described preferred embodiments the chemokine is selected from the group consisting of PF-4, IL-8, MGSA, IP-10, NAP-2, MCP-1, MIP-1α, MIP-1β and RANTES.

According to still further features in the described preferred embodiments the cytokine is selected from the group consisting of IL-3, TNFα, TNFβ, GM-CSF and IFNγ.

According to still further features in the described preferred embodiments the degradative enzyme is selected from the group consisting of elastase, lipoprotein lipase and cathepsin G.

According to still further features in the described preferred embodiments the condition is selected from the group consisting of angiogenesis, cell proliferation, tumor cell proliferation, invasion of circulating tumor cells, metastases, inflammatory disorders and autoimmune conditions.

The present invention successfully addresses the shortcomings of the presently known configurations by providing a heparanase activity neutralizing monoclonal anti-heparanase antibody, method for its preparation, identification and characterization, pharmaceutical composition including same and the use of same for treating various medical conditions.

BRIEF DESCRIPTION OF THE DRAWINGS

The invention herein described, by way of example only, with reference to the accompanying drawings, wherein:

FIG. 1 demonstrates epitope mapping of monoclonal antibodies HP-130 and HP-239 according to the present invention. The different polypeptides (as indicated below) were fractionated on SDS-PAGE and transferred to a nitrocellulose membrane (Schleicher and Schuell). The membrane was reacted with either antibody HP-130 or HP-239 as indicated above. Lane 1, cell extracts containing a heparanase segment of 414 amino acids of the heparanase open reading frame (amino acids 130–543, SEQ ID NO: 1). Lane 2, cell extracts containing a heparanase segment of 314 amino acids of the heparanase open reading frame (amino acids 230–543, SEQ ID NO:1). Lane 3, cell extracts containing a heparanase segment of 176 amino acids of the heparanase open reading frame (amino acids 368–543, SEQ ID NO:1). Lane 4, cell extracts containing heparanase segment of 79 amino acids of the heparanase open reading frame (amino acids 465–543, SEQ ID NO:1). Lane 5, cell extracts containing heparanase segment of 229 amino acids of the heparanase open reading frame (amino acids 1–229, SEQ ID NO: 1). Lane 6, cell extracts containing heparanase segment of 347 amino acids of the heparanase open reading frame (amino acids 1–347, SEQ ID NO:1). Lane 7, cell extracts containing heparanase segment of 465 amino acids of the heparanase open reading frame (amino acids 1–465, SEQ ID NO:1). Lane 8, size markers (Bio-Rad).

DESCRIPTION OF THE PREFERRED EMBODIMENTS

The present invention is of a heparanase activity anti-heparanase monoclonal antibody which can be used to inhibit heparanase catalytic activity. Specifically, the present invention can be used to treat conditions associated with heparanase catalytic activity.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The experimental results obtained while reducing the present invention to practice and which are presented herein teach anti-heparanase monoclonal antibodies which can be used as therapeutic heparanase activity neutralizing antibodies.

The neutralizing antibodies can be used to inhibit heparanase activity, which, as a result, modulate the function of HSPG associated biologic effector molecules.

These effector molecules include: growth factors, such as, but not limited to, HGH, FGF and VEGF; chemokines, such as, but not limited to, PF-4, IL-8, MGSA, IP-10, NAP-2, MCP-1, MIP-1α, MIP-1β and RANTES; cytokines, such as, but not limited to, IL-3, TNFα, TNFβ, GM-CSF and IFNγ; and degradative enzymes, such as, but not limited to, eiastase, lipoprotein lipase and cathepsin G (31).

Neutralization of heparanase activity may thus, for example, prevent angiogenesis caused due to the activation of bFGF, and allow inhibition of cell proliferation, such as tumor cell proliferation.

Neutralization of heparanase activity may also be used to inhibit degradation of the basement membrane, which allows invasion of circulating tumor cells, and thus prevent metastasis.

In a similar mechanism, neutralization of heparanase activity may prevent from activated cells of the immune system to leave circulation and thus inhibit elicitation of both inflammatory disorders and autoimmune responses.

Besides the use of neutralizing antibodies for therapeutics, these antibodies may be used for research purposes, to allow better understanding of the role of heparanase in different processes.

For future clinical applications, the anti-heparanase monoclonal antibodies may be improved, through a humanization process, to overcome the human antibody to mouse antibody response. Rapid new strategies have been developed recently for antibody humanization (25, 26, 27) which may be applied for this antibody. These technologies maintain the affinity, and retain the antigen and epitope specificity of the original antibody (26, 27).

Thus, in accordance with one aspect of the teachings of the present invention there is provided a monoclonal antibody elicited by a heparanase protein or an immunogenical portion thereof. The monoclonal antibody of the present invention is capable not only of specific binding to, or interacting with, heparanase, it also specifically inhibits or neutralizes heparanase catalytic activity.

According to another aspect of the present invention there is provided a pharmaceutical composition which includes, as an active ingredient thereof, a monoclonal antibody elicited by a heparanase protein or an immunogenical portion thereof and a pharmaceutical acceptable carrier. The monoclonal antibody specifically inhibits heparanase activity.

As used herein in the specification and in the claims section below, the phrase "heparanase catalytic activity" or its equivalent "heparanase activity" refers to an animal endoglycosidase hydrolyzing activity which is specific for heparin or heparan sulfate proteoglycan substrates, as opposed to the activity of bacterial enzymes (heparinase I, II and III) which degrade heparin or heparan sulfate by means of β-elimination. Heparanase activity which is inhibited or neutralized according to the present invention can be of either recombinant or natural heparanase. Such activity is disclosed, for example, in U.S. patent application Ser. Nos. 09/071,739; 09/071,618; and 09/113,168, which are incorporated by reference as if fully set forth herein.

As used herein in the specification and in the claims section below, the term "protein" also refers to a polypeptide. The protein can be recombinant or natural. The protein can be a portion of the full recombinant or natural protein. The protein preparation used for vaccination can be crude, partially purified or highly purified.

As used herein in the specification and in the claims section below, the term "antibody" refers to any monoclonal or polyclonal immunoglobulin, or a fragment of an immunoglobin such as sFv (single chain antigen binding protein), Fab1 or Fab2. The immunoglobulin could also be a "humanized" antibody, in which, for example animal (say murine) variable regions are fused to human constant regions, or in which murine complementarity-determining regions are grafted onto a human antibody structure (Wilder, R. B. et al., J. Clin. Oncol., 14:1383–1400, 1996). Unlike, for example, animal derived antibodies, "humanized" antibodies often do not undergo an undesirable reaction with the immune system of the subject. The terms "sFv" and "single chain antigen binding protein" refer to a type of a fragment of an immunoglobulin, an example of which is sFv CC49 (Larson, S. M. et al., Cancer, 80:2458–68, 1997). Additional detail concerning antibody humanization are found in references 25–27 which are incorporated as if fully set forth herein.

Thus, as used herein in the specification and in the claims section below, the term "humanized" and its derivatives refers to an antibody which includes any percent above zero and up to 100% of human antibody material, in an amount and composition sufficient to render such an antibody less likely to be immunogenic when administered to a human being. It is being understood that the term "humanized" reads also on human derived antibodies or on antibodies derived from non human cells genetically engineered to include functional parts of the human immune system coding genes, which therefore produce antibodies which are fully human.

As used herein in the specification and in the claims section below, the term "inhibit" and its derivatives refers to suppress or restrain from free expression of activity.

The term "neutralize" and its derivatives are specifically used herein in context of a single heparanase molecule which can be either neutralized or active.

According to a preferred embodiment of the present invention at least about 60–70%, preferably, at least about, 70–80%, more preferably, at least about 80–90% of the heparanase activity is abolished by the inhibition when about 1 to about 1–40, preferably about 2–30, more preferably about 4–20, most preferably about 5–15 ratio of heparanase to antibody is realized, either, in situ, in loco, in vivo or in vitro.

As specifically shown in the Examples section hereinunder, the neutralizing antibody binds specifically the C'-terminal portion of heparanase, indication that the C'-terminal portion of heparanase is involved in its catalytic activity.

As used herein in the specification and in the claims section below, the term C'-terminal portion refers to a continuous or discontinuous epitope or epitopes involving amino acids derived from any location or locations, either continuous or dispersed, along the 100 C'-terminal amino acids of heparanase. Continuous or discontinuous epitopes typically include 3–8 continues or discontinuous amino acids.

According to another aspect of the present invention there is provided an in vivo or in vitro method of preparing a heparanase activity neutralizing monoclonal anti-heparanase antibody. The method is effected by implementing the following method steps, in which, in a first step, cells (either in vivo or in vitro) capable of producing antibodies are exposed to a heparanase protein or an immonogenical part thereof to thereby generate antibody producing cells. In a subsequent step the antibody producing cells are fused with myeloma cells to thereby generate a plurality of hybridoma cells, each producing monoclonal antibodies. Then the plurality of monoclonal antibodies are screened to identify a monoclonal antibody which specifically inhibits heparanase activity. The later step is typically preceded by first screening for a monoclonal antibody which specifically binds heparanase.

According to a preferred embodiment of the present invention the method further comprising the step of humanizing the heparanase activity neutralizing monoclonal anti-heparanase antibody. Such a humanizing step can be effected following the procedures described hereinabove, which are known in the art. Typically humanizing antibodies involves genetically modifying non-human cells to include functional genes and sequences derived from the human immune system gene complex or the system as a whole, which is performed prior to exposing the cells to an immunogen, as described in the above method steps.

According to yet another aspect of the present invention there is provided a method of treating a condition associated with heparanase expression. The method is effected by administering a neparanase activity neutralizing monoclonal anti-heparanase antibody to a patient suffering from the condition, wherein the monoclonal anti-heparanase antibody serves for neutralizing heparanase catalytic activity.

As used herein in the specification and in the claims section below, the term "treat" or treating and their derivatives includes substantially inhibiting, slowing or reversing the progression of a condition, substantially ameliorating clinical symptoms of a condition or substantially preventing the appearance of clinical symptoms of a condition.

As used herein in the specification and in the claims section below, the phrase "associated with heparanase expression" refers to conditions which at least partly depend on expression of heparanase. It is being understood that the expression of heparanase under many such conditions can be normal, yet inhibition thereof in such conditions will result in improvement of the affected individual.

Thus, the condition can be related to altered function of a HSPG associated biological effector molecule, such as, but not limited to, growth factors, chemokines, cytokines and degradative enzymes. The condition can be, or involve, angiogenesis, tumor cell proliferation, invasion of circulating tumor cells, metastases, inflammatory disorders and/or autoimmune conditions.

Additional objects, advantages, and novel features of the present invention will become apparent to one ordinarily skilled in the art upon examination of the following examples, which are not intended to be limiting.

Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Procedures

Materials: Heparin SEPHAROSE was purchased from Pharmacia. 1,9-Dimethylmethylene Blue was purchased from Aldrich (Cat No. 34108).

Monoclonal antibody production: Six to eight weeks old female Balb/C mice were each immunized intradermally with 50 µg (50 µl) recombinant heparanase (prepared and purified essentially as described in U.S. patent application Ser. No. 09/071,618, which is incorporated by reference as if fully set forth herein) emulsified in 50 µl PBS complete Freund's adjuvant. Two to three weeks later the same amount of the emulsion was injected subcutaneously or intradermally at multiple sites in incomplete Freund's adjuvant. After 3 weeks 25 µg antigen in aqueous solution was injected intrapertonealy. Seven to ten days later, animals were bled and the titer of the relevant antibodies was determined. Three to four weeks after the last boost, one or two animals were injected intraperitonealy with 20 µg of soluble antigen (in PBS) and 3–4 days later spleens were removed.

Fusion and cloning of monoclonal antibodies: The spleens of immunized mice were ground, splenocytes were harvested and fused with NSO myeloma cells by adding 41% PEG. Hybridoma cells were grown in HAT-selective DMEM growth media containing 15% (v/v) HS (Beit Haemek), 2 mM glutamine, Pen-Strep-Nystatin solution (Penicillin:10000 units/ml, Streptomycin:10 mg/ml, Nystatin:1250 units/ml), at 37° C. in 8% $CO_2$. Hybridoma cells were cloned by limiting dilution. Hybridomas producing Mabs to human heparanase were identified by reactivity with solid-phase immobilized human heparanase (native and denatured (ELISA)).

Cell culturing: Hybridoma cells were cultured in T-175 flasks (Corning Costar, Cat. No. 430824) in a $CO_2$-enriched incubator (8%), at 37° C. in DMEM medium (Beit Haemek, Israel) supplemented with 10% horse serum (Beit-Haemek Cat. No. 04-124-1A). Culture volume was 80 ml.

Production of antibodies by the starvation method (28): Cultures reaching cell density of $2\times10^6$ cells/ml or higher, were used for the production of antibodies. Cells were removed from the flasks by pipetting and were centrifuged at 1,000 rpm for 5 minutes in order to pellet the cells. The cell pellets were suspended in basal DMEM (with no serum added) and centrifuged at 1,000 rpm for 5 minutes. This procedure was repeated once more and the cell pellets were suspended in the original volume of basal DMEM medium. Cell suspension was plated into new T-175 flasks and placed inside the incubator. After 48 hours, cells were pelleted by centrifugation at 3,500 rpm for 10 minutes. Culture supernatants were filtered through 0.2 micron pore-size filter (Nalgene, Cat. No. 156-4020) and were supplemented with 0.05% sodium azide. Culture supernatants were kept refrigerated until purification.

Purification of monoclonal antibodies: Purification was performed by affinity chromatography using Protein G (28, 14). 2.5 ml of Protein G SEPHAROSE 4 Fast Flow (Pharmacia Cat. No. 17-0618-01) were used to pack each column (BioRad, Cat. No. 737-1517). The flow rate for packing the columns was 4 ml/min. The column was equilibrated with 100 ml of PBS pH 7.2. Culture supernatants (filtered and supplemented with sodium azide as described above) were loaded on the column at a flow rate of 1 ml/minute. After loading, column was washed with 80 ml of PBS pH 7.2 at a flow rate of 0.4 ml/minute. Elution was done with 12 ml of 0.1 M Glycine-HCl buffer, pH 2.7, at a flow rate of 1 ml/minute. One ml fractions were collected into tubes containing 0.3 ml of 1M Tris pH 9.0. Column was further washed after elution with 50 ml of the elution buffer at a flow rate of 4 ml/min. Column was then regenerated by passing 50 ml of regeneration buffer (0.1 M Glycine-HCl buffer pH 2.5). After regeneration, the column was immediately neutralized with 100 ml of PBS pH 7.2, 0.1% sodium azide was added and the column which was thereafter stored in the refrigerator.

Eluted fractions were analyzed for protein content using the Bradford protein determination method. According to the results obtained, 4–6 fractions were pooled and dialyzed (Spectrum dialysis tubing, MWCO 6,000–8,000, Cat. No. 132653) three times against 500 ml of PBS buffer pH 7.2 with 0.05% sodium azide, or against PBS pH 7.2 with 1% thimerosal (Sigma, Cat. No. T-8784) added. After dialysis samples were stored at 4° C.

Western blots: Proteins were separated on 4–20%, polyacrylamid ready gradient gels (Novex). Following electrophoresis proteins were transferred to Hybond-P nylon membrane (Amershem) (350 mA/100V for 90 minutes). Membranes were blocked in TBS containing 0.02% Tween 20 and 5% skim milk for 1–16 hours and then incubated with antisera diluted in the same blocking solution. Blots were then washed in TBS-Tween, incubated with appropriate HRP-conjugated anti mouse/anti rabbit IgG, and developed using ECL reagents (Amersham) according to the manufacturer's instructions.

Epitope mapping: A 1.7 Kb fragment of hpa cDNA (a hpa cDNA cloned in pfastBacHTA, see U.S. patent application Ser. No. 08/922,170, which is incorporated by reference as if fully set forth herein) was digested by various restriction enzymes to create serial deletions from both the 3' and the 5' ends of the heparanase open reading frame (ORF) as follows.

3' deletions: EcoRI-BstEII fragment, encoding amino acids 1–465, deletion of an NdeI-XbaI fragment generating an ORF of 347 amino acids (1–347) and a deletion of AflII-XbaI fragment generating an ORF of 229 amino acids (1–229).

5' deletions: BamHI-XhoI fragment encoding 414 amino acids, (130–543), an AflII-XhoI fragment encoding 314 amino acids (230–543), an NdeI-XhoI fragment encoding 176 amino acids 368–543) and a BstEII-XhoI fragment encoding 79 amino acids of the heparanase open reading frame (465–543).

The heparanase segments were expressed in Baculovirus expression system, essentially as described in U.S. patent application Ser. No. 09/071,618. The fragments were subcloned into the vector pfastBacHT to generate His tagged fusion constructs. Recombinant baculovirus containing the various fragments were generated using the Bac to Bac system (GibcoBRL) according to the manufacturer recommendations. Extracts of Sf21 cells expressing various segments of heparanase protein were analyzed. The recombinant heparanase segments were detected by Western blots.

Heparanase activity assay: 100 µl heparin SEPHAROSE (50% suspension in double distilled water) were incubated in 0.5 ml eppendorf tubes placed on a head-over-tail shaker (37° C., 17 hours) with enzyme preparations in reaction mixtures containing 20 mM Phosphate citrate buffer pH 5.4, 1 mM $CaCl_2$ and 1 mM NaCl, in a final yolume of 200 □1. Enzyme preparations used were either purified recombinant heparanase expressed in insect cells (U.S. patent application Ser. No. 09/071,618), or heparanase partially purified from human placenta (30). At the end of the incubation period, the samples were centrifuged for 2 minutes at 1000 rpm, and the products released, to the supernatant due to the heparanase activity were analyzed using the calorimetric assay-Dimethyhiiethylene Blue as described in U.S. patent application No. 09/113,168, which is incorporated by reference as if fully set forth herein.

Dimethylmethylene Blue assay (DMB): Supernatants (100 µl) were transferred to plastic cuvettes. The samples were diluted to 0.5 ml with PBS plus 1% BSA. 1,9-Dimethylmethylene blue (32 mg dissolved in 5 ml ethanol and diluted to 1 liter with forrmate buffer) (0.5ml) was added to each sample. Absorbance of the samples was determined using a spectrophotometer (Cary 100, Varian) at 530 nm. To each sample a control to which the enzyme was added at the end of the incubation time, was included.

Experimental Results

Epitope Mapping: As part of the task of characterizing purified monoclonal antibodies, it is necessary to determine whether individual antibodies raised against the same antigen bind to identical or overlapping epitopes.

A linear method was used to map the epitope recognized by each antibody within the heparanase protein. Serial deletions were made and assayed for the production of fragments that can be recognized by each antibody. In practice, this method can only localize the binding site to a small region.

Supernatants from two monoclonal antibodies, HP-130 and HP-239 were examined by western blot for reactivity with various segments of recombinant heparanase expressed in Baculovirus infected insect cells.

Figure 1:
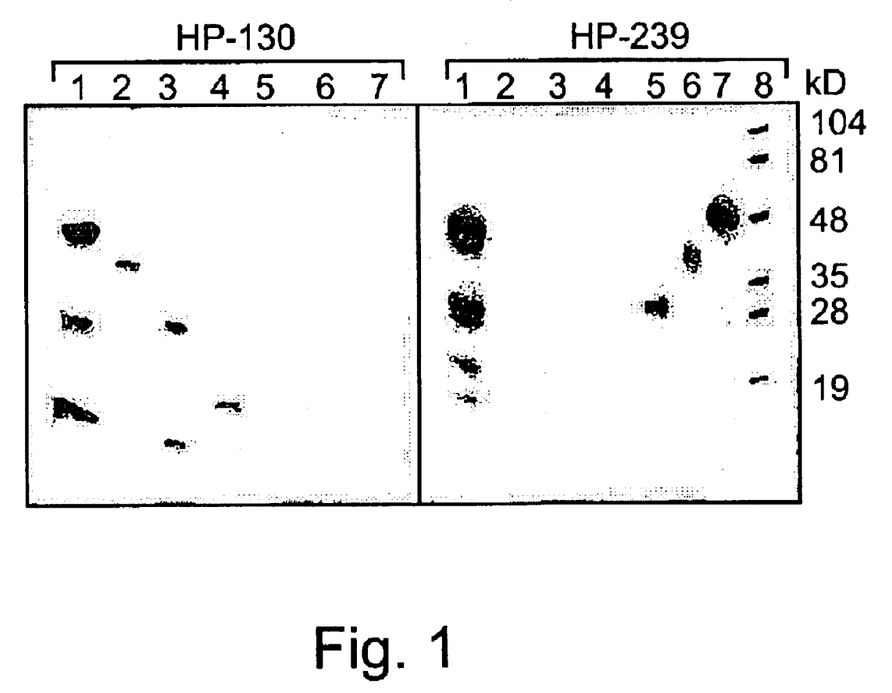

As can be seen in FIG. 1, monoclonal antibody HP-130 recognized a segment of 79 amino acids at the C-terminus of the heparanase open reading frame (amino acids 465–543). The monoclonal antibody HP-239 recognized an internal epitope localized to amino acids 130–230.

Neutralization of recombinant heparanase expressed in insect cells: The ability of the different monoclonal antibodies to inhibit the activity of a recombinant heparanase expressed in insect cells was examined. Reactions mixtures containing 5 µg of enzyme were pre-incubated for 30 min at room temperature, with increasing amounts of antibodies (25 to 170 µg, forming molar ratios of 1:1.7 to 1:10 enzyme to antibody, for antibody HP-130, and 12.5 to 250 µg, forming molar ratios of 1:0.85 to 1:18.5, for antibody HP-239).

Following pre-incubation, heparanase activity was determined using DMB assay as described in experimental procedures. The percent of activity measured in the presence of each antibody amount, as compared to the activity of a control reaction lacking the antibodies is presented in FIG. 2.

Figure 2:
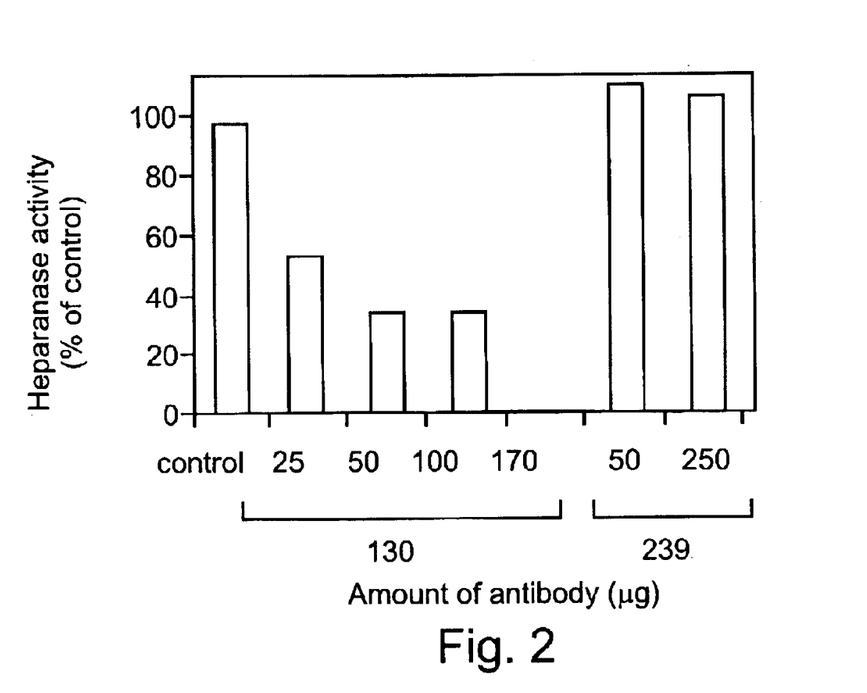
FIG. 2 demonstrates neutralization of recombinant heparanase expressed in insect cells with monoclonal antibodies. Heparanase activity after pre-incubation of the recombinant heparanase expressed in insect cells, with increasing amounts (as indicated under each bar) of antibody HP-130 (130) and antibody HP-239 (239). The percent of activity is calculated from the control reaction, pre-incubated in the absence of the antibody.

As can be seen in FIG. 2, monoclonal antibody HP-130 which is directed against the C-terminus of the heparanase enzyme, was capable of almost completely inhibiting recombinant heparanase activity at a molar ratio of 1:10.

Pre-incubation of the heparanase with increasing concentrations of antibody resulted in dose-dependent inhibition of the activity (FIG. 2). The other antibody examined, HP-239, which is directed against an internal epitope of the heparanase, caused no inhibition of heparanase activity even at a higher ratio of antibody to enzyme (1:18.5), as compared to the ratio that gave almost complete inhibition with antibody HP-130. These two antibodies were prepared and purified in the same manner, indicating that inhibition of heparanase activity by antibody HP-130 is specific. The molar ratios of enzyme to antibody in which antibody HP-130 inhibited heparanase activity are similar to molar ratios reported in the literature that are used for neutralization of other enzymes (21, 22). The fact that an antibody formed against the C-terminus of the enzyme was capable of almost completely inhibiting its activity, while an antibody directed against an internal epitope had absolutely no effect could suggest the possible role of the C-terminus in the heparanase activity, and may indicate the possibility that other antibodies directed against this region may also have a neutralizing effect on heparanase activity.

Neutralization of natural heparanase activity purified from human placenta: To examine the possibility whether the monoclonal antibody HP-30 could inhibit a natural heparanase in the same manner that they inhibit the recombinant enzyme, a similar experiment was designed as described above with heparanase purified from human placenta.

As the specific activity of the natural enzyme is much higher than its recombinant counterpart, 5 ng of enzyme were used for this experiment. The activity of this amount of enzyme in the linear range of the DMB heparanase activity assay.

The enzyme was pre-incubated with increasing amounts of antibody while maintaining similar molar ratios as used for the recombinant enzyme (20 to 450 ng of antibody HP-130 forming molar ratios of 1:4 to 1:95 enzyme to antibody, and 225 ng of antibody HP-239 forming a molar ratio of 1:20). The percent of activity remained in the presence of each antibody amount, as compared to the activity of a control reaction lacking the antibodies is presented in FIG. 3.

Figure 3:
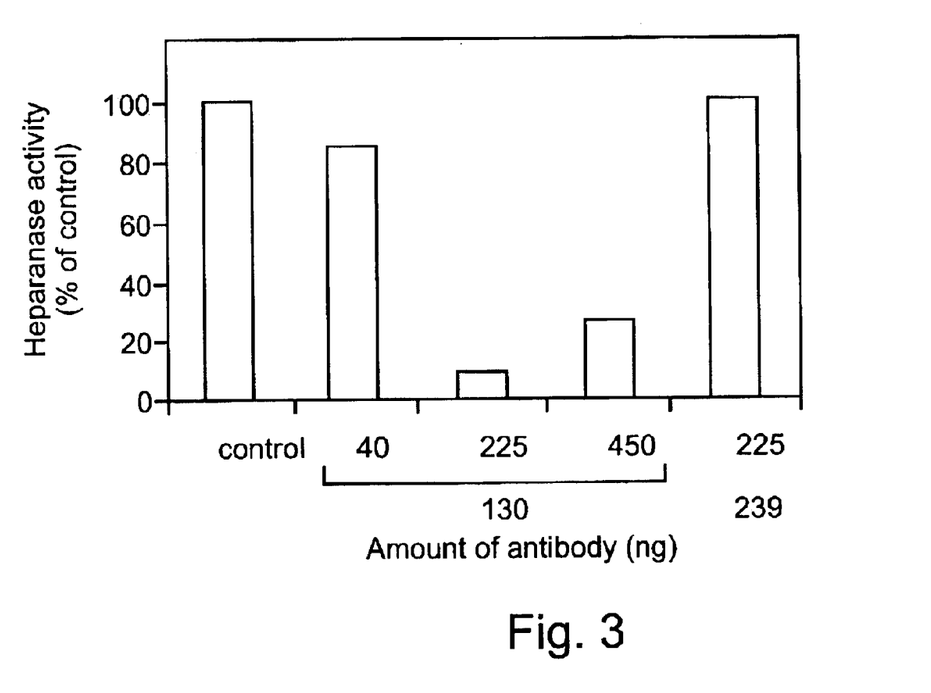
FIG. 3 demonstrates neutralization of natural heparanase purified from human-placenta with monoclonal antibodies. Heparanase activity after pre-incubation of neparanase isoiated from human placenta with increasing amounts (as indicated under each bar) of antibody HP-130 (130) and antibody HP-239 (239). The percent of activity is calculated from the control reaction, pre-incubated in the absence of the antibody.

As shown in FIG. 3, 225 ng of antibody HP-130 were capable of inhibiting 90% of the heparanase activity purified from human placenta. This amount of antibody forms a molar ratio of 1:20 enzyme to antibody, similar to the ratio that almost completely inhibited the recombinant heparanase expressed in insect cells. Antibody HP-239, on the other hand, used at the same molar ratio, did not have any effect on heparanase activity. The ability of monoclonal antibody HP-130 to inhibit a natural human heparanase enzyme exemplifies the possibility to use recombinant heparanase to screen for neutralizing agents against naturally occurring enzymes.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

References Cited

1. Wight, T. N., Kinsella, M. G., and Qwarnstromn, E. E. (1992). The role of proteoglycans in ceii adhesion, migration and proliferatioin. Curr. Opin. Cell Biol., 4, 793–801.
2. Jackson, R. L., Busch, S. J., and Cardin, A. L. (1991). Glycosaminoglycans: Molecular properties, protein interactions and role in physiological processes. Physiol. Rev., 71, 481–539.
3. Wight, T. N. (1989). Cell biology of arterial proteoglycans. Arteriosclerosis, 9, 1–20.
4. Kjellen, L., and Lindahl, U. (1991). Proteoglycans: structures and interactions. Annu. Rev. Biochem., 60, 443–475.
5. Ruoslahti, E., and Yamaguchi, Y. (1991). Proteoglycans as modulators of growth factor activities. Cell, 64, 867–869.
6. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.
7. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127.
8. Vlodavsky, I., Mohsen, M., Lider, O., Ishai-Michaeli, R., Ekre, H.-P., Svahn, C. M., Vigoda, M., and Peretz, T. (1995). Inhibition of tumor metastasis by heparanase inhibiting species of heparin. Invasion & Metastasis, 14: 290–302.
9. Nakajima, M., Irimura, T., and Nicolson, G. L. (1988). Heparanase and tumor metastasis. J. Cell. Biochem., 36, 157–167.
10. Liotta, L. A., Rao, C. N., and Barsky, S. H. (1983). Tumor invasion and the extracellular matrix. Lab. Invest., 49, 639–649.

11. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711.
12. Vlodavsky, I., Ishai-Michaeli, R., Bar-Ner, M., Fridman, R., Horowitz, A. T., Fuks, Z. and Biran, S. Involvement of heparanase in tumor metastasis and angiogenesis. Is. J. Med. 24:464–470, 1988.
13. Parish, C. R., Coombe, D. R., Jakobsen, K. B., and Underwood, P. A. (1987). Evidence that sulfated polysaccharides inhibit tumor metastasis by blocking tumor cell-derived heparanase. Int. J. Cancer, 40, 511–517.
14. Bjorck L, Kronvall G. Purification and some properties of streptococcal protein G, a novel IgG-binding reagent. J. Immunol 1984; 133: 969–974.
15. Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci., 16, 268–271.
16. Campbell, K. H., Rennick, R. E., Kalevich, S. G., and Campbell, G. R. (1992) Exp. Cell Res. 200, 156–167.
17. Lider, O., Baharav, E., Mekori, Y., Miller, T., Naparstek, Y., Vlodavsky, I. and Cohen, I. R. Suppression of experimental autoimmune diseases and prolongation of allograft survival by treatment of animals with heparinoid inhibitors of T lymphocyte heparanase. J. Clin. Invest. 83:752–756, 1989.
18. Thunberg L, Backstrom G, Grundberg H, Risenfield J, Lindahl U: Themolecular size of the antithrombin-binding sequein heparin. FEBS Lett 1980; 117:203–206.
19. Goldberg R L, Kolibas, L M : An improved method for determining proteoglycans synthesized by chondrocytes in culture. Connective Tissue Res. 1990; 24: 265–275.
20. Hudson P J; Recombinant antibody fragment. Curr. Opin. Biothecnol. 1998; 4: 395–402.
21. Schoepe H, Wieler L H, Bauerfeind R, Schlapp T, Potschka H, Hehnen H, Baljer G. Neutralization of hemolytic and mouse lethal activities of C. perfringens alpha-toxin need simultaneous blockage of two epitopes by monoclonal antibodies. Microbial Pathogenesis 1997; 23:1–10.
22. Chiba J, Nakano M, Suzuki Y, Aoyama K, Ohba T, Yasuda A, Kojima A, Kurata T; Generation of neutralizing antibody to the reverse transcriptase of human immunodeficiency virus type 1 by immunizing of mice with an infectious vaccinia virus recombinant. J. Immunological Methods 1997; 207: 53–60.
23. Wong J F. Monoclonal antibodies: Therapeutic applications grow in promise and number. Genetic Engineering News 1998; July: 23,49.
24. Sherman-Gold R. Monoclonal antibodies: The evolution from '80s magic bullets to mature, mainstream applications as clinical therapeutics. Genetic Engineering News 1997; August: 4,35.
25. Danheiser S L. Rituxin leads line of hopeful Mab therapies, yet FDA still has bulk manufacture concerns. Genetic Engineering News 1997; October: 1,6,33,38.
26. Rader C, Chersh D A, Baras C F 3rd. A phage display approach for rapid antibody humanization: designed combinatorial V gene libraries. Proc. Natl Acad. Sci. 1998 95: 8910–8915.
27. Mateo C, Moreno E, Amour K, Lombardero J, Harris W, Perez R. Humanization of a mouse monoclonal antibody that blocks the epidermal growth factor receptor: recovery antagonistic activity. Immunothechnology 1997; 3:71–81.
28. Iscove N N, Melchers F. Complete replacement of serum by albumin, transferrin, and soybean lipid in cultures of lipopolysaccharide-reactive B lymphocytes. J. Exp. Med. 147: 923–933.
29. Kronvall G. A surface component in group A,C, and G streptococci with non-immune reactivity for immunoglobulin G. J. Immunol. 1973; 111:1401–1406.
30. Goshen R, Hochberg A A, Korner G, Levy E, Ishai-Michaeli R, Elkin M, de Groot M, Vlodavsky I. Purification and characterization of placental heparanase and its expression by cultured cytotrophoblasts. Mol. Human Reproduction 1996; 2:679–684.
31. Selvan R S, Ihrcke N S, Platt J L. Heparan sulfate in immune responses. Annals New York Acad. Sci. 1996; 797:127–139.

What is claimed is:

1. A method of reducing heparanase catalytic activity in-vivo comprising administering to a subject a monoclonal anti-heparanase antibody, wherein:
   (a) said monoclonal anti-heparanase antibody specifically inhibits heparanase catalytic activity in-vitro;
   (b) said monoclonal anti-heparanase antibody is elicited by at least one epitope of a heparanase protein having an amino acid sequence as set forth in SEQ ID NO:1; and
   (c) said anti-heparanase monoclonal antibody binds specifically to an epitope involving amino acid residues along the 100 C'-terminal amino acid residues of said heparanase protein;
   thereby reducing heparanase activity in-vivo.

2. The method of claim 1, wherein said subject is suffering from a heparanase-related condition associated with altered function of a heparan sulfate proteoglycans (HSPG) associated biological effector molecule.

3. The method of claim 2, wherein said HSPG associated biological effector molecule is selected from the group consisting of a growth factor, a chemokine, a cytokine and a degradative enzyme.

4. The method of claim 3, wherein said growth factor is vascular endothelial growth factor (VEGF).

5. The method of claim 2, wherein said condition is angiogenesis.

6. The method of claim 1, wherein said monoclonal anti-heparanase antibody is humanized or human.

* * * * *